United States Patent [19]

Gurbel et al.

[11] Patent Number: 5,295,959
[45] Date of Patent: Mar. 22, 1994

[54] AUTOPERFUSION DILATATION CATHETER HAVING A BONDED CHANNEL

[75] Inventors: Paul A. Gurbel; R. David Anderson, both of Baltimore, Md.

[73] Assignee: Medtronic, Inc., Minneapolis, Minn.

[21] Appl. No.: 850,638

[22] Filed: Mar. 13, 1992

[51] Int. Cl.⁵ .............................................. A61M 29/00
[52] U.S. Cl. ...................................... 604/96; 604/103; 606/194
[58] Field of Search ................................ 606/191–192, 606/194; 604/96, 101, 103

[56] References Cited

U.S. PATENT DOCUMENTS

| | | |
|---|---|---|
| 4,498,473 | 2/1985 | Gereg . |
| 4,527,549 | 7/1985 | Gabbay .................... 606/192 X |
| 4,581,017 | 4/1986 | Sabota . |
| 4,681,564 | 7/1987 | Landreneau . |
| 4,737,147 | 4/1988 | Ferrando et al. . |
| 4,762,130 | 8/1988 | Fogarty et al. . |
| 4,787,388 | 11/1988 | Hofmann . |
| 4,790,315 | 12/1988 | Mueller, Jr. et al. . |
| 4,881,939 | 11/1989 | Newman . |
| 4,909,252 | 3/1990 | Goldberger . |
| 4,934,786 | 6/1990 | Krauter . |
| 4,950,232 | 8/1990 | Ruzicka et al. . |
| 4,983,167 | 1/1991 | Sabota . |
| 5,078,685 | 1/1992 | Colliver ......................... 604/96 |
| 5,116,318 | 5/1992 | Hillstead ........................ 604/96 |

OTHER PUBLICATIONS

Adams, Daniel, "PRCA Balloon Materials, Their Characteristics and Impact on Catheter Selection", Technical Notes.

Primary Examiner—C. Fred Rosenbaum
Assistant Examiner—Corrine Maglione
Attorney, Agent, or Firm—Mullen, White, Zelano and Branigan

[57] ABSTRACT

An autoperfusion dilatation catheter useful in angioplasty comprises a conventional catheter shaft and an inflatable balloon. The catheter is designed such that the balloon, when inflated, has an outer surface relief-structure whereby when this outer surface is fully inflated and exerts pressure on the inner surface of a blood vessel, blood continues to flow between the outer surface of the balloon and the blood vessel surface. Preferably, the relief structure is a channel formed in the outer surface of the balloon by the pressure of a band attached to the catheter and which presses against the outer surface of the balloon.

12 Claims, 4 Drawing Sheets

AUTOPERFUSION DILATATION CATHETER HAVING A BONDED CHANNEL

BACKGROUND OF THE INVENTION

This invention relates to a dilatation balloon catheter, useful for medical procedures such as angioplasty, which permits fluid flow, e.g., perfusion (blood flow), around the outer peripheral surfaces of the balloon when the latter is inflated and in contact with surrounding surfaces such as the inner lining of the walls or the atheromatous plaque of a blood vessel (artery or vein) such as a coronary artery, as well as to methods of making and using the same.

Dilatation balloon catheters are well known and used daily in medical practice for life-saving coronary angioplasty procedures wherein atheromatous plaque adhering to a blood vessel wall and blocking or restricting blood flow therein is compressed to reestablish and/or increase blood flow by dilating the lumen of the artery. Compression of the plaque is effected by inflation of the balloon while it is positioned in the blood vessel so that it is located adjacent to and surrounded by the plaque.

Depending on the location of the plaque and the size of the blood vessel, a pre-shaped and pre-dimensioned catheter having a pre-shaped and pre-dimensioned inflatable balloon adhered thereto (by fluid seals), is selected. The interior of the catheter typically possesses two lengthwise channels (lumen): one for fluid inflation of the generally tubular shaped balloon (e.g., to an inflated diameter of 1-7 mm, larger or smaller diameters being possible) with which it is in sealed communication, and the other for insertion of a guidewire running the full length of the catheter to assist in positioning it during a medical operation.

Many such catheters have been disclosed as well as details of construction, methods of preparation and methods of use. See, e.g., the disclosures of U.S. Pat. No. Reissue 33,166 and U.S. Pat. Nos. 4,169,263, 4,323,071, 4,411,055, 4,571,240, 4,573,470, 4,582,181, 4,597,755, 4,616,653, 4,619,263, 4,638,805, 4,641,654, 4,664,113, 4,692,200, 4,748,982, 4,771,776, 4,771,778, 4,775,371, 4,782,834, 4,790,315 and 4,793,350, all of whose entire disclosures are incorporated by reference herein.

One of these references addresses the problem of occlusion of blood flow during an angioplasty procedure. See U.S. Pat. No. 4,790,315. As noted therein (column 1), during an angioplasty procedure, blood flow is cut off during the period of time the balloon remains inflated. As a result, the myocardium becomes ischemic with potentially serious consequences and the patient experiences chest pain. Thus, inflation duration must necessarily be relatively short, e.g., typically less than 180 seconds, commonly less than 150 seconds. Longer inflation times would be very desirable since better plaque compression could be effected, thereby increasing the probability of a successful procedure. Moreover, higher risk patients (e.g., those for whom any duration of blood occlusion in the particular vessel involved is an especially dangerous event) for whom angioplasty is contraindicated could have access to this valuable procedure.

U.S. Pat. No. 4,790,315 attempts to solve the blood flow occlusion problem by providing a lumen or channel inside the length of the body of the catheter between the proximal and distal ends of the catheter shaft. A plurality of openings in the side wall of the catheter on the proximal and distal sides of the balloon provide blood flow past the balloon through this lumen. However, this design has siqnificant drawbaoks. For example, the blood flow provided is relatively small, e.g., only 60-70 ml/min., significantly less than normal flow (e.g., 100-120 ml/min. for coronary arteries). Moreover, the profile of this design (i.e., total cross-sectional diameter of the catheter shaft) is much larger than that of a normal catheter due to the need for a large lumen to accommodate the resultant blood flow volume. Such a high profile catheter itself represents a danger, e.g., even of occluding or seriously impeding blood flow, for many patients, significantly lessening the applicability of its limited advantages to both a wide cross-section of patients and to various complexities of obstructions. Moreover, even where it can be employed, this prior art catheter is bulky and makes it difficult to cross blockages and/or access lesions in distal vasculature.

Thus, there remains a need for an improved dilatation balloon catheter, e.g., which permits continued blood flow when the balloon is inflated in a blood vessel, has an optimally low profile, and enhances patient safety and availability of angioplasty and other balloon catheter-based procedures to a wider class of patients, inter alia.

SUMMARY OF THE INVENTION

This invention relates to an autoperfusion dilatation balloon catheter useful in angioplasty comprising a catheter shaft and, mounted on said shaft, an inflatable non-elastomeric balloon having proximal and distal ends disposed along the length of said catheter shaft, said balloon when inflated having an outer surface relief-structure (or topography) whereby when said balloon is fully inflated and exerts pressure on the inner surface of a blood vessel in which blood is flowing, blood continues flowing between said outer surface of said balloon and said inner surface of a blood vessel.

In another embodiment, an autoperfusion dilatation balloon catheter useful in angioplasty comprises a catheter shaft; mounted on said shaft, an inflatable non-elastomeric balloon having proximal and distal ends disposed along the length of said catheter shaft and having an outer surface; said outer surface being capable, when said balloon is fully inflated inside a blood vessel which has an inner surface and blood flowing therein, of exerting pressure on said inner blood vessel surface; and said balloon further comprising means for permitting blood to continue flowing between said proximal and distal ends.

In preferred aspects: the relief-structure comprises at least one channel extending along the outer surface of the balloon from its proximal end to its distal end; the channel is disposed around the outer surface of the balloon in a helical-like or spiral-like pattern or is disposed longitudinally along only one side of said balloon and not around the latter; there are plural channels for blood flow, e.g., 2 (as in FIG. 3), 3, 4, etc.; the channels are formed by compressing the balloon's surface against the catheter shaft on a line corresponding to the helical-like, longitudinal or other configuration of the channel, whereby when the balloon is inflated in use, the channel is formed along such line, i.e., the balloon becomes inflated along the surfaces which are not held in contact with the catheter shaft; the compression of the balloon against the catheter shaft is achieved by a band fixed at each end to the catheter shaft and mounted over the balloon surface along the mentioned line, wherein the band is wire-like or ribbon-like in shape; the band remains in contact with the outer surface of the catheter shaft, thereby holding the balloon (tightly) to the latter or the band is disposed in a recessed groove in the catheter shaft, thereby holding the balloon tightly to the latter but avoiding protrusion of the band beyond the outer surface of the catheter shaft; the outer surface of the balloon is covered by a radially-expandable, pressure distribution sleeve which, when the balloon is inflated, expands in response to the pressure of inflation of the balloon to exert pressure evenly along the exterior surface of the sleeve against the wall of a blood vessel into which the catheter has been inserted; the channel is preformed in the balloon during thermoplastic molding of the latter (not requiring a band such as a wire or ribbon for channel formation); the channel(s) in the balloon provide a blood flow having a volume typically of at least 90–100 ml/min., preferably 80 to 100%, of normal blood flow; the autoperfusion balloon catheter of this invention is used in performing angioplasty procedures or as an inflatable stent in repairing damaged blood vessel walls, and in other procedures conducted in blood vessels.

This invention also relates to an autoperfusion dilatation catheter balloon useful in angioplasty which is inflatable and non-elastomeric, said balloon when inflated having an outer surface relief-structure whereby when said balloon is fully inflated and exerts pressure on the inner surface of a blood vessel in which blood is flowing, blood continues flowing between said outer surface of said balloon and said inner surface of said blood vessel.

By the term "non-elastomeric" is meant that the material from which the balloon wall is composed is made from a substance, e.g., typically a polymeric material, which is not scientifically classified as an elastomer by those skilled in the polymer or angioplasty balloon fields. An "elastomer" is conventionally defined as a polymer, typically a thermosetting polymer, having properties similar to those of vulcanized natural rubber, i.e., the ability to be stretched to at least twice its original length and to retract very rapidly to approximately the original length when released (Hawley's Condensed Chemical Dictionary, 11th Edition, Ed. Sax et al., Van Nostrand-Reinhold Co., 1987; McGraw-Hill Dictionary of Scientific and Technical Terms, 4th Edition, Ed. Parker, McGraw-Hill Book Company, 1989). Thus, the non-elastomeric balloons of this invention do not possess type angioplasty catheters, the balloon materials suitable for use in this invention, upon inflation to pressures in the range of 10–15 atmospheres or lower, will inflate to a certain volume (diameter) ± about 10–15%, irrespective of the precise inflation pressure within the balloon's recommended range. Rather than elastomerically continuing to expand or stretch beyond such a volume, such balloons instead will rupture or permanently deform when exposed to higher pressures. Thus, a conventional angioplasty balloon is rated for burst strengths which are lower than those which would be available if elastomers such as vulcanized natural rubber were used to fabricate an identically dimensioned balloon. Accordingly, an identical elastomeric balloon will continue to increase in size (volume and overall diameter) throughout such a pressure range to an extent many times greater than the ±10–15% estimate mentioned above. While eventually also rupturing, it will do so much less abruptly than the conventional non-elastomeric balloons of this invention and at higher pressures. From another perspective, the non-elastomeric balloons of this invention, typical in angioplasty catheters, will have a distention profile (diameter vs. pressure curve) significantly different from that of an elastomeric balloon. The former, for instance, will typically flatten out significantly at higher pressures prior to rupture, whereas the latter typically will burst more precipitously. Thus, "non-elastomeric," in the context of this invention, does not refer to materials having absolutely no elastomeric nature; rather, it refers to materials such as those discussed in Adams, below, which are much less elastomeric than the usual elastomers such as vulcanized natural rubber and similar synthetic rubbers. Moreover, when conventional angioplasty balloons are deflated, they just flatten out; they do not "elastically recoil" to the center shaft as would an elastomer.

As discussed by Adams below, precise and easy control of the diameter of a balloon is an important requirement for use in a catheter. A balloon having a wall structure comprising only its wall polymeric material, e.g., with no underlying support structure, if made of elastomeric material, would be very difficult to control in the necessary fashion. For example, rather than a diameter change (in the mm range) of 10–20% over a pressure change, e.g., 2–6 atm, much larger values would be achieved.

Typical non-elastomeric polymeric materials suitable for use in preparing the balloons of this invention and typical properties of the same are fully conventional and are disclosed, e.g., in "PTCA Balloon Materials, Their Characteristics and Impact on Catheter Selection," Daniel O. Adams, Technical Notes, available from Sci. Med. Life Sciences, Inc., 1300 Co. Rd. 6, Plymouth, MN 53441, which entire disclosure is incorporated by reference herein. These include the materials well known to those of skill in the art for preparation of conventional angioplasty balloon materials, e.g., those mentioned in the references incorporated by reference above, including polyolefins (e.g., polyethylene (ACS), irradiated polyethylene, polyolefin copolymer (SciMed)), polyvinyl chloride (USCI), polyesters (e.g., polyethylene terephthalate (USCI)), etc. These can be heat-shrinkable when the balloon is to be sealably adhered to the catheter shaft by thermoplastic heating effects. Of course, the balloon can also be conventionally sealably attached to the shaft by use of an adhesive. The balloon can also be sealed proximally and distally by a thin wire ribbon as was common in earlier angioplasty balloon designs. Alternatively, it can be formed by the newer molding techniques which allow it to be held in place proximally by a wire wrapped around the catheter body and distally by heatwelding the balloon to the inner catheter body that passes through it.

The balloons typically have very thin, single-layer walls made of the mentioned non-elastomeric materials and are of great strength. They do not utilize any substructural support components to maintain rigidity, size, shape or a built-in inflation limitation.

When the balloons are conventionally inflated during an angioplasty or other procedure, typically using an X-ray contrast medium (e.g., triiodinated benzenes), in Y the range of 10-15 atmospheres (lower or higher pressures also being applicable), they will inflate to a predetermined size (volume and outer diameter) and shape (typically tubular) chosen in conformance with considerations of the nature of the procedure being performed, the size of the catheter, the sizes of the vessel wall and any occlusion therein, etc. The balloon will provide a high rigidity (stiffness) sufficient for compressing an atheromatous mass. The non-elastomeric nature of the balloon is important in this regard so that there can be good precision in predetermining the nature of the pressure which will be exerted on any particular occlusion in any particular blood vessel.

All other components of the catheter per se can be fully conventional in design and construction. Typically, most components of the catheter shaft will be composed of polymeric materials whose important properties can be freely designed using conventional considerations of polymer technology, e.g., as discussed in the references incorporated by reference above. Metallic components are also fully conventional.

The catheter of this invention can also comprise other conventional design aspects, such as containing at least two ports or lumen through the center of the catheter shaft. Once such lumen communicates with and allows for inflation of the balloon in all embodiments of this invention. Another port typically traverses the center of the catheter body or tube for guidewire usage or for delivery of medicants or sample withdrawal. Other ports or lumen may also be included and may exit at various points along the catheter or distal to the balloon. Similarly, additional ports may also be included which exit within the balloon to facilitate more rapid inflation/deflation or for use for delivery of various contrast agents for various diagnostic modalities, typically X-ray.

The wall thicknesses of the balloons suitable for use in this invention will be in the same range as for conventional catheters. Similarly, balloon shapes will be the same. Furthermore, standard inflation pressures will be employed. In other words, inclusion of the relief-structure in the outer surface of the balloon will not materially affect other aspects of balloon design, inflation or use.

The catheter of this invention may be termed a multipurpose autoperfusion angioplasty catheter (MAAC) in view of its capability of permitting blood flow in a blood vessel when the balloon is inflated and in contact with the vessel walls. It is a multipurpose device, not only because it accommodates all of the prior art uses for angioplasty catheters, but also because it enables additional applications to more dangerous procedures and/or to patients involving higher risk factors for whom such procedures were heretofore contraindicated.

The autoperfusion characteristics of the catheter of this invention can be achieved by inclusion in the outer surface of the balloon of a relief-structure, e.g., of one or more channels extending from the distal end to the proximal end of the balloon. These channels can proceed longitudinally from proximal to distal end without encircling the balloon, can partially encircle the same or can fully encircle the same in the pattern of a spiral or helix. These channels can be formed in conventional nonelastomeric angioplasty balloons by the simple superposition thereon of a small compression band in the configuration of the desired channel pattern. The band can comprise a wire, e.g., a metal or plastic wire (e.g., <1/16" diameter, e.g., 0.01–0.06 inch, typically) or a metal or plastic ribbon (also <1/16" thickness, e.g., typically 0.01–0.06 inch, ×1-2 mm in width). Of course, when the band is made of a polymeric material, the latter will also be non-elastomeric. Other non-elastic materials of similar size and characteristics can also be used.

By fixing the (spiral) compression band to the catheter body at or beyond the proximal and distal ends of the angioplasty balloon, (spiral) channels will be formed and maintained in the outer surface of the balloon when the latter is inflated. All that is required is that the band be secured to the shaft sufficiently tightly that the portions of the balloon thereunder will not inflate normally but rather will be held in contact with or near contact with the catheter shaft, thereby providing the desired channels. The compression band can be made of or coated with radio-lucent or radio-opaque material depending upon the procedure involved. Optionally, the compression band(s) fixed to the catheter body can lay on top of the outer surface of the catheter shaft or can be positioned flush with the outer surface of the catheter shaft by provision in the latter of a recessed groove into which the compression band will fit snugly while maintaining the balloon surface in contact with the shaft. The latter embodiment provides for a catheter tube having very low profile, i.e., essentially the same profile as a tube without the additional band, approaching or meeting the overall low profile of current non- o autoperfusion angioplasty catheters.

Alternatively, the channels can be introduced into the outer surface of the balloon during conventional thermoplastic molding processing. A mold having a configuration which approximates the nature of the channels desired in the outer surface of the balloon can be used during heat treatment formation of the (inflated) balloon. Alternatively, the balloon can be wrapped with a band as described above prior to heat treatment in inflated condition in a conventional mold in order to set into the walls thereof preformed channels. After the balloon structure is finally set at the end of the processing, upon inflation, the balloon will conform to the (spiral) channel structure of the mold providing a function equivalent to that of the channels formed by the compressive force of the bands as described above. Such thermoplastic molding techniques are fully conventional.

In either the compression band or other molding embodiments, the specific characteristics of the channel(s) can be varied to achieve any desired flow characteristics. Thus, the width, depth and shape of the channels, as well as the number of channels, can be varied to increase or decrease, facilitate or hinder the nature of the blood flow achievable. Typical satisfactory channel cross-sectional areas can be routinely determined and normally will be in the range of 0.05 to 2 $mm^2$. Furthermore, the nature of the flow can also be adjusted by adjusting the period of spiral-type channels. Channel cross-sectional shape can routinely be varied, e.g., by corresponding choice of band shape or mold wall shape; thus, shapes from rounded (e.g., spherical, ellipsoidal, etc.) to angular (e.g., rectangular, square-like, polygonal, etc.) can be used. Similarly, a channel can maintain the same configuration from proximate to distal end or can be varied in shape along its length. It is even possible for a single channel to branch into two or more channels along the length thereof. Similarly, overall balloon design can accommodate the same variability in inflation characteristics as currently available with conventional balloon catheter designs, e.g., outer balloon diameter, balloon rigidity, balloon strength, pressure range for maximum inflation, etc.

In another embodiment of the multi-purpose autoperfusion angioplasty catheter of this invention, a radially-expandable, pressure distribution sleeve (sheath) can be disposed around or fitted over the outer surface of the relief-structure-containing balloon of this invention. This will be useful in instances where an entire 360° of complete and continuous radial force is necessary or desired to achieve a given effect during a particular angioplasty or other procedure. In this embodiment, when the balloon is inflated, the pressure which would otherwise be directly exerted against the inner surfaces of a vessel wall or an atheromatous plaque, instead will be inserted against the inner surface of the typically tubular sleeve, thereby expanding the latter radially. The latter, in turn, will exert a radial force all along its continuous outer surface, thereby providing 360° of continuous radial force against the inner surface of the vessel.

Such a sleeve will typically have the shape of a tube having a wall thickness of 0.005–0.015 mm, smaller and larger thicknesses being applicable, and may be composed of a sheet of elastomeric material to effectively transfer the radial forces as described. It could also be fabricated from a fine wire, woven fabric or other mesh that expands/contracts. The mesh material could be non-elastomeric where the wire mesh or woven fabric mesh design provides the necessary expansion/contraction. It can also be made of elastomeric material. The open cell, mesh-type design has the advantage that the mesh itself will provide flow characteristics, thereby assisting in maintaining the channels open. Materials for the sleeve may be selected from among the many synthetic elastomeric, non-elastomeric, fabric, metallic materials available whose properties can be conventionally routinely designed to achieve tensile strengths, elongations at rupture, stiffnesses, hardnesses, etc., as needed. The diameter of the tube (sheath), its design and its materials will typically be chosen such that the elastomeric or expandable sheath will recoil or collapse when the balloon is deflated to nearly the size of the deflated balloon/catheter. In all cases, it will be preferred that the tube will have an outer diameter narrower than the smallest opening provided by the most severe atheromatous plaque encountered in the subject vessel. The inner diameter of the tube will be chosen to be 0.01–0.020 mm greater than the maximum outer diameter of the catheter, taking into account the deflated balloon. The sheath can be removable whereupon it is easily placed over the balloon when desired during a procedure. Alternatively, the sheath can be fixedly attached to the outer surface of the balloon, if desired, e.g., at the outermost points of the inflated balloon such that the channels remain unobstructed to an extent that blood flow therethrough is not materially or unacceptably hindered.

An equivalent of the sheath-containing embodiment of this invention, especially where the sheath is bonded to the outer surfaces of the balloon above the channels, is an embodiment of this invention wherein instead of or in addition to an outer surface relief structure, the balloon comprises one or more, flow-corresponding through, tubular channels formed in the interior of the balloon between its outer surface and the catheter shaft or at its center and generally running parallel to the shaft. These inner channels provide a pathway for blood flow through the balloon and have walls which are part of the balloon and seal the channel from the inside of the balloon. Such balloon structures can be manufactured by conventional thermoplastic and/or thermosetting forming techniques. In one design, the balloon itself has a shape like a hollow, elongated tube or cylinder where the walls of the balloon are double layered containing inflating liquid therebetween and are located along the walls of the cylinder, thereby forming an annular balloon with a hollow tubular channel at its center through which blood can flow. The balloon double-layer walls are inflatably/deflatably attached to a catheter shaft lumen by one or more inflation tubes. The latter can be sealably attached to the balloon walls and/or shaft by conventional methods including heat-sealing techniques and/or using adhesives. In another design, a balloon has its conventional overall shape but one, two or more hollow, longitudinal, tubular channels are formed therein for blood flow.

All embodiments of the MAAC of this invention possess the advantage over conventional angioplasty catheters, including the conventional perfusion angioplasty catheter described above, of being able to provide distal blood vessel perfusion of a highly advantageous nature while the balloon remains inflated. Thus, the length of time that the balloon can remain in inflated condition is lengthened from typical values of 5–10 minutes for non-perfusion catheters to values for this invention of <1 to >24 hours. The latter time periods represent a significant improvement over the times available with the current perfusion catheter, typically minutes to a few hours maximum, although on occasion the conventional perfusion catheter has been used for 24 hours.

Another significant advantage of the MAAC of this invention vis-a-vis the conventional perfusion catheter is the low profile provided Unlike the conventional perfusion catheter, there is no need for a catheter shaft of higher volume than that of non-perfusion catheters since blood flow occurs not through the catheter shaft but rather around the balloon. Thus, the MAAC catheter can have essentially the same profiles as are available with conventional catheters (e.g., 0.5–1.25 mm). The MAAC catheter can be made as small as I mm in diameter including its non-elastomeric balloon thickness, allowing for extremely low profiles while deflated and excellent crossability with respect even to tight blockages. Simultaneously, the catheter of this invention can utilize the usual fixed diameter balloons (selectable at will) with the advantageous new flow characteristics provided by this invention when inflated.

Available blood flow in conventional perfusion catheters is in the range of 60–70 ml/min. The catheter of this invention, however, will easily approach nearly normal flow rates (at least for coronary arteries) of around 100 ml/min. Typically, the blood flow provided by this invention will have a volume rate of at least 80% of normal blood flow, preferably 90–100% thereof, when the balloon is fully inflated in a blood vessel and is exerting its normal pressure on the inner surface of the latter during an angioplasty procedure.

Further advantageously, the large flow channels in the balloon of this invention will avoid thrombosis and consequent hemostasis, a potential problem in current perfusion technology.

The methods of using the MAAC of this invention will be essentially in accordance with conventional procedures except for the ability to take advantage of the new desirable characteristics provided by the embodiments of this invention, e.g., as described herein. Thus, when used as an autoperfusion catheter, a device of this invention will be guided into place in the deflated mode within a blood vessel constricted by a clot and/or plaque, optionally using a conventional guidewire which is placed through the body of the catheter via one of its lumen. The catheter of this invention will then be inflated to displace the vessel and the obstruction while maintaining distal vessel perfusion through the relief-structure in the balloon (with or without a radially-expandable sleeve thereover). Once the desired opening of the vessel blockage has been achieved, the balloon is then conventionally deflated and removed.

Another advantage of this invention is that the guidewire approach to placement of the catheter can be replaced by a simple fixed wire attached to the distal catheter tip. Much of guidewire usage in current angioplasty is prompted or necessitated by the occasional need for rapid replacement of one angioplasty balloon for another of a different size or for a perfusion balloon. The use of the MAAC catheter with a fixed wire tip will often obviate the need for guidewire use since it is an angioplasty balloon and autoperfusion device combined in one.

Another advantage of this invention is that the increased safety provided by the perfusion occurring during an angioplasty or other procedure makes such procedures available to a wider class of patients including those heretofore considered to be at too high a risk. Furthermore, for any patient undergoing such a procedure, the device of this invention will significantly lower risk by maintaining perfusion during the operation, thereby decreasing chances of the myocardium becoming ischemic or patients experiencing chest pain and other like adverse reactions. Furthermore, the MAAC catheter is easily usable in all patient subgroups and should render the already well-established therapeutic techniques which utilize balloon catheters even safer.

One of the more common complications of percutaneous transluminal coronary angioplasty (PTCA) is the so-called dissection of a blood vessel wall. Current technology allows for "tacking" up of the inner vessel damage but only for a limited time due to the finite downstream perfusion available in conventional devices and the risk of thrombosis. The catheter of this invention, on the other hand, provides an inflatable stent that may be maintained in its inflated position almost indefinitely (e.g., for hours, e.g., 24 or more hours if desired) in view of the autoperfusion characteristics it possesses. This will significantly enhance the chances for success of the "tacking" procedure. The latter can be further facilitated by heparin coating the balloon with currently available technology. Use of the MAAC as an inflatable stent decreases the risk of ischemia or infarction while enhancing chances for successful repair of the dissected vessel wall.

Other than as described herein, the catheter of this invention can be used in fully conventional fashion.

BRIEF DESCRIPTION OF THE DRAWINGS

Various other objects, features and attendant advantages of the present invention will be more fully appreciated as the same becomes better understood when considered in conjunction with the accompanying drawing, in which like reference characters designate the same or similar parts throughout the several views, and wherein.

DETAILED DESCRIPTION OF THE PREFERRED EMBODIMENTS

Figure 1:
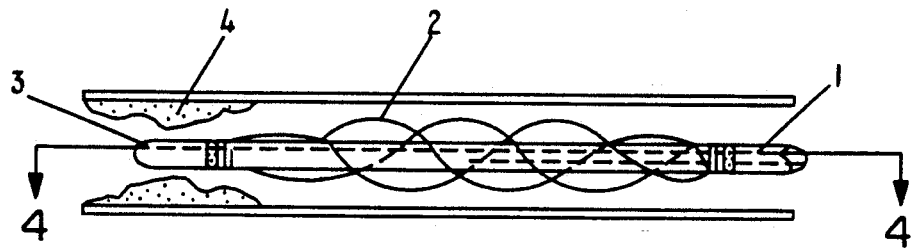
FIG. 1 shows a perspective view of a first embodiment of the multi-purpose autoperfusion angioplasty catheter (MAAC) 1 with its balloon 2 inflated and tip 3 juxtaposed between two walls of an atheromatous plaque 4.
Figure 2:
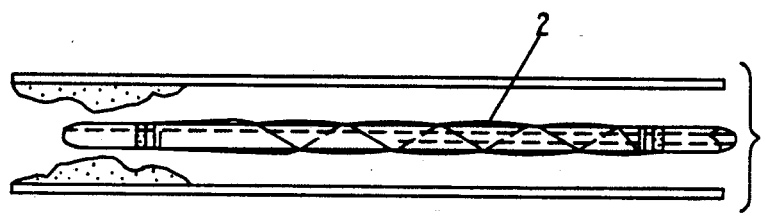
FIG. 2 shows a view similar to FIG. 1 but with the non-elastomeric balloon 2 deflated.
Figure 3:
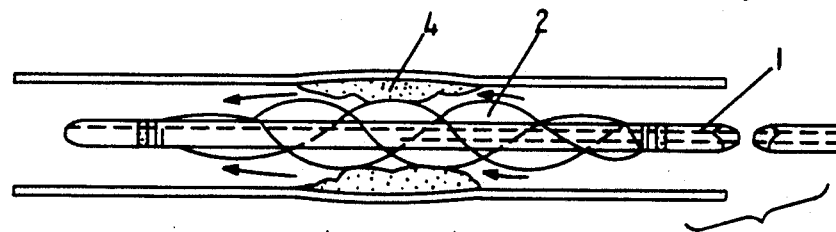
FIG. 3 shows a view of the FIG. 1 configuration with the body of the MAAC 1 placed transversely through the plaque 4 and its balloon 2 inflated demonstrating flow-through characteristics while providing expansion of plaque and blood vessel lumen.
Figure 4:
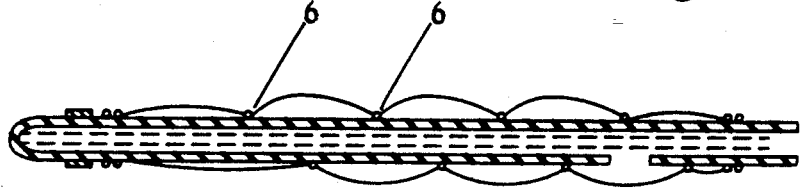
FIG. 4 shows an enlarged cross-sectional view of the MAAC at section 4—4 of FIG. 1.
Figure 5:
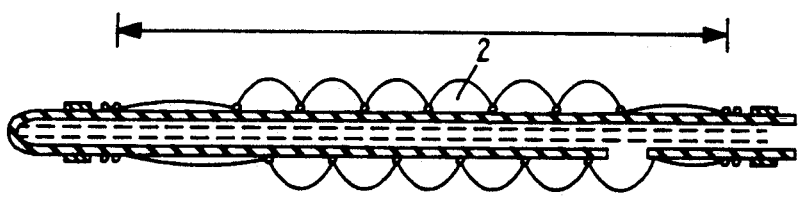
FIG. 5 shows an enlarged cross-sectional view of a variant of the MAAC with a different spiral period of the balloon 2.
Figure 6:
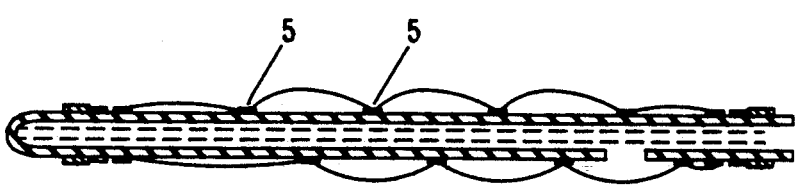
FIG. 6 shows a view of a FIG. 1 type embodiment utilizing a spiral compression ribbon 5 in lieu of the spiral compression wire 6 of FIG. 4.
Figure 7:
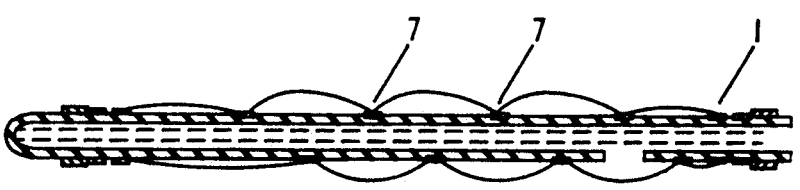
FIG. 7 shows an enlarged cross-sectional view of a recessed spiral compression band (a ribbon in this case) 7 into the catheter body or tube.
Figure 8:
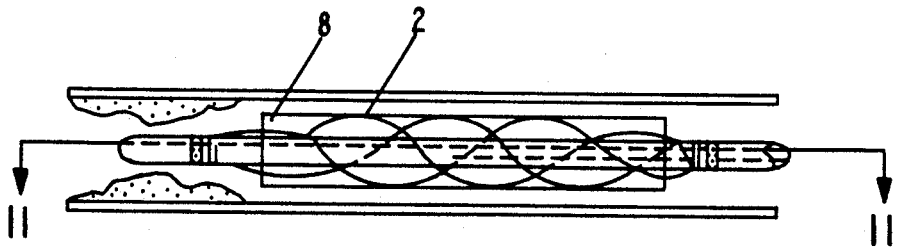
FIG. 8 shows a view of the MAAC demonstrating an expandable radial distribution sleeve 8 encompassing much of the balloon for 360° of radially distributed force.
Figure 9:
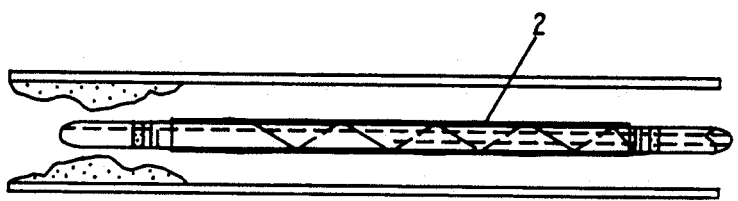
FIG. 9 is a schematic of the embodiment of FIG. 8 but with the balloon 2 in the deflated, very low profile position.
Figure 10:
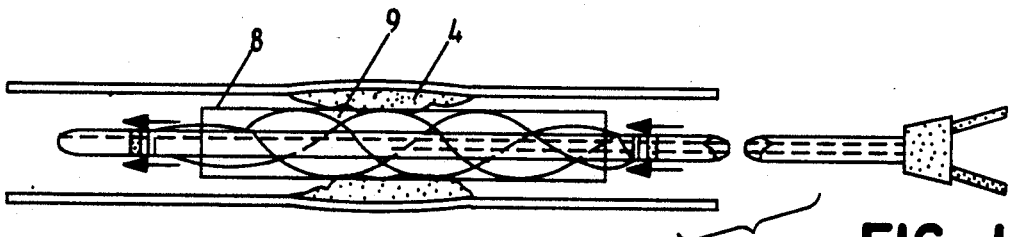
FIG. 10 is a perspective of the MAAC shown in FIG. 8 with the radial distribution sleeve, inflated inside the atheromatous plaque, which demonstrates 360° of radial force with vessel lumen and obstruction dilated while allowing distal perfusion in channel 9.
Figure 11:
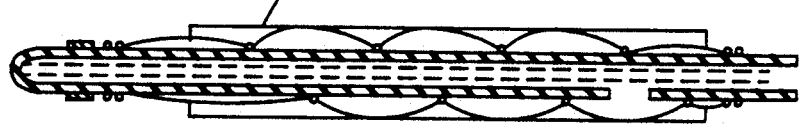
FIG. 11 is an enlarged cross-sectional view of the MAAC in FIG. 8 at section 11—11 including the radial distribution sleeve 8 in the inflated mode.
Figure 12:
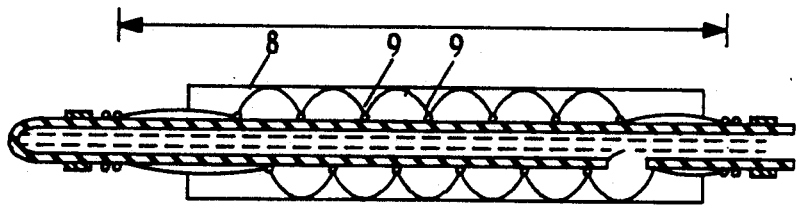
FIG. 12 is another enlarged cross-sectional view of the MAAC fitted with a radial distribution sleeve 8 but illustrating alternative periodicity of the spiral channels 9 for different applications and plaque morphologies.
Figure 13:
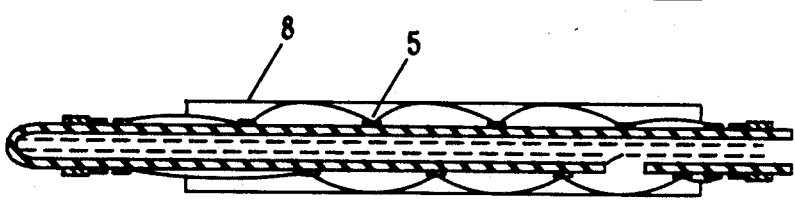
FIG. 13 is a view of the MAAC similar to FIG. 6 but including the spiral compression ribbon 5 and the radial distribution sleeve 8.
Figure 14:
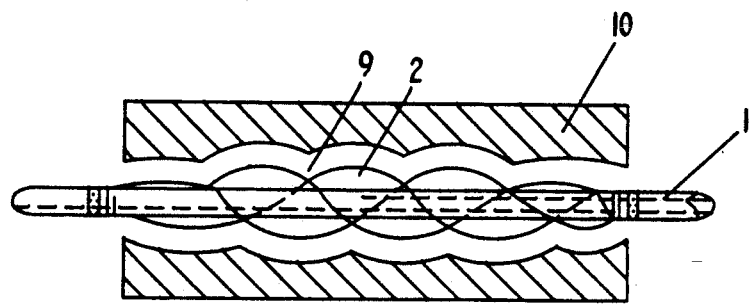
FIG. 14 shows another variant of the MAAC that is manufactured without a spiral compression band; it is displayed with its mold 10 that allows the channels 9 to be fitted to the balloon 2 at the time of initial expansion under temperature elevation. The spiral valleys may or may not be ultrasonically welded to the catheter body or tube 1.
Figure 15:
FIG. 15 shows another view of the MAAC of FIG. 14 in the deflated, very low profile state.
Figure 16:
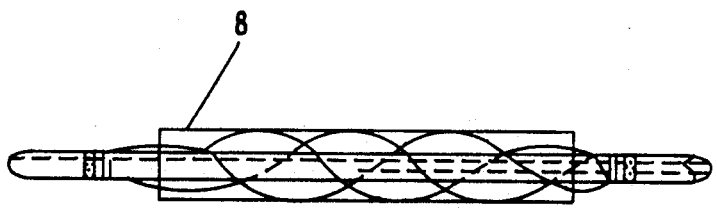
FIG. 16 shows a variant similar to the MAAC shown in FIG. 14 but including the radial distribution sleeve 8.
Figure 17:
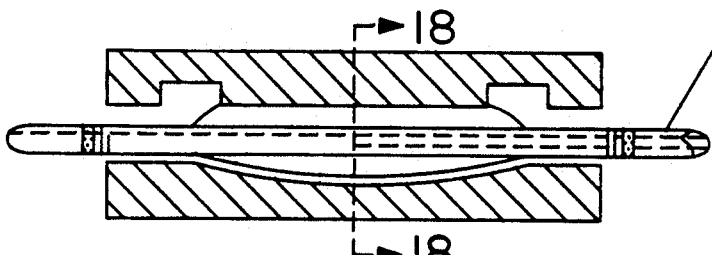
FIG. 17 shows an additional variant of a MAAC which allows a single lengthwise blood flow channel 9, parallel to the catheter body or tube 1; this would be accomplished by a similar molding technique as shown in FIG. 14.
Figure 18:
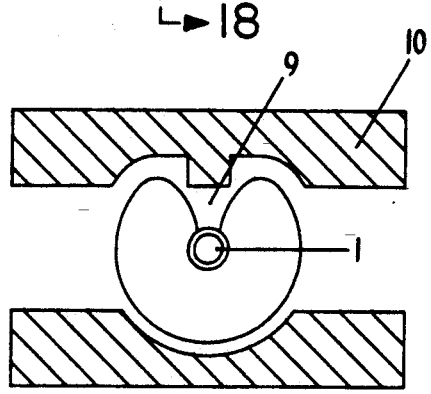
FIG. 18 shows a radial cross-section of the MAAC catheter shown in FIG. 17 with a cross-section of the mold 10 as well.
Figure 19:
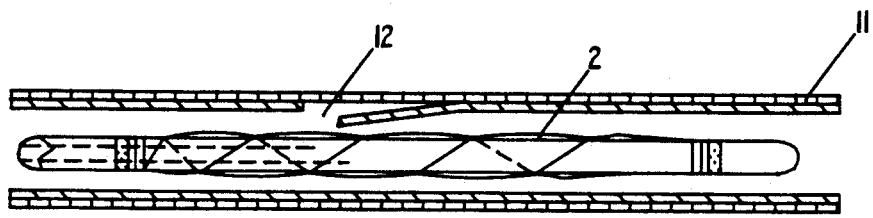
FIG. 19 illustrates the MAAC in the lumen of a vessel 11 with a dissection 12 of its intima; the balloon 2 is deflated.
Figure 20:
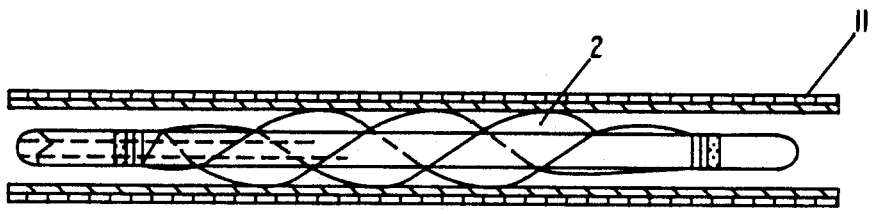
FIG. 20 illustrates the MAAC of FIG. 19 with the balloon 2 inflated and the damaged vessel wall reduced and repositioned while still allowing distal perfusion in the channels of the MAAC; this is the inflatable stent usage of the MAAC.
Figure 21:
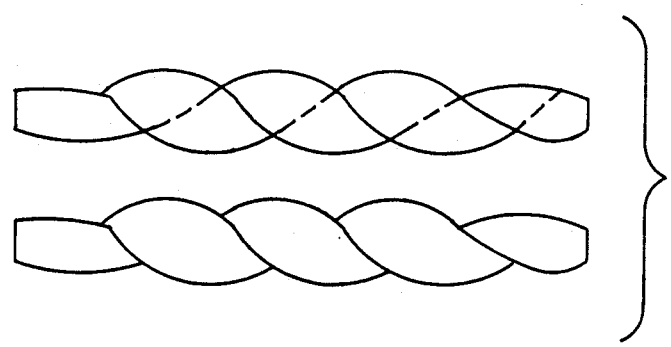
FIG. 21 contains plane views of a MAAC.
Figure 22:
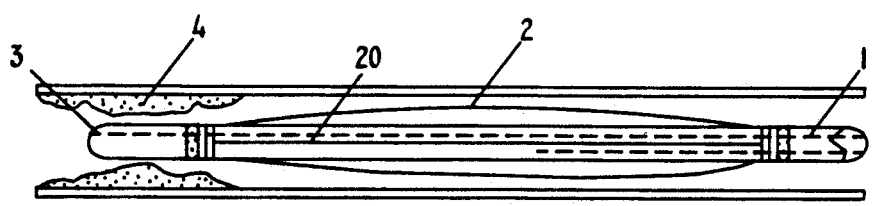
FIG. 22 contains a view similar to FIG. 1 but with one channel disposed along only one side of the balloon and not around the balloon.

FIG. 1 shows a perspective view of a first embodiment of the multi-purpose autoperfusion angioplasty catheter (MAAC) 1 with its balloon 2 inflated and tip 3 juxtaposed between two walls of an atheromatous plaque 4. Channels are formed by compressing the balloon 2 surface against the catheter shaft 1 on a line corresponding to the helical-like, longitudinal or other configuration of the channel, whereby when the balloon 2 is inflated in use, the channel is formed along such line, i.e., the balloon 2 becomes inflated along the surfaces which are not held in contact with the catheter shaft 1. The compression of the balloon 2 against the catheter shaft 1 is achieved by a band fixed at each end to the catheter shaft 1 and mounted over the balloon 2 surface along the mentioned line, wherein the band is wire-like as shown by 6 in FIG. 4 or ribbon-like as shown in FIG. 6 at 5. FIG. 2 shows a view similar to FIG. 1 but with the non-elastomeric balloon 2 deflated. FIG. 3 shows a view of the FIG. 1 configuration with the body of the MAAC 1 placed transversely through the plaque 4 and its balloon 2 inflated demonstrating flow-through characteristics while providing expansion of plaque and blood vessel lumen. FIG. 4 shows an enlarged cross-sectional view, including the compression wire 6, of the MAAC at section 4—4 of FIG. 1. FIG. 5 shows an enlarged cross-sectional view of a variant of the MAAC with a different spiral period of the balloon 2. FIG. 6 shows a view of a FIG. 1 type embodiment utilizing a spiral compression ribbon 5 in lieu of the spiral compression wire 6 of FIG. 4. FIG. 7 shows an enlarged cross-sectional view of a recessed spiral compression band (a ribbon in this case) 7 into the catheter body or tube. FIG. 8 shows a view of the MAAC demonstrating an expandable radial distribution sleeve 8 encompassing much of the balloon for 360 degrees of radially distributed force. FIG. 9 is a schematic of the embodiment of FIG. 8 but with the balloon 2 in the deflated, very low profile position. FIG. 10 is a perspective of the MAAC shown in FIG. 8 with the radial distribution sleeve 8, inflated inside the atheromatous plaque 4 with demonstrates 360 degrees of radial force with vessel lumen and obstruction dilated while allowing distal perfusion in channel 9. FIG. 11 is an enlarged cross-sectional view of the MAAC in FIG. 8 at section 11—11 including the radial distribution sleeve 8 in the inflated mode. FIG. 12 is another enlarged cross-sectional view of the MAAC fitted with the radial distribution sleeve 8 but illustrates alternative periodicity of the spiral channel 9 for different applications and plaque morphologies. FIG. 13 is a view of the MAAC similar to FIG. 6 but including the spiral compression ribbon 5 and the radial distribution sleeve 8. FIG. 14 shows another variant of the MAAC that is manufactured without a spiral compression band. It is displayed with its mold 10 that allows the channels 9 to be fitted to the balloon 2 at the time of initial expansion under temperature elevation. The spiral valleys may or may not be ultrasonically welded to the catheter body or tube 1. FIG. 15 shows another view of the MAAC of FIG. 14 in the deflated, very low profile state. FIG. 16 shows a variant similar to the MAAC shown in FIG. 14 but including the radial distribution sleeve 8. FIG. 17 shows an additional variant of a MAAC which allows a single lengthwise blood flow channel 9, parallel to the catheter body or tube 1. This would be accomplished by a similar molding technique as shown in FIG. 14. FIG. 18 shows a radial cross-section of the MAAC catheter shown in FIG. 17 with a cross-section of the mold 10 as well. FIG. 19 illustrates the MAAC in the lumen of a vessel 11 with a dissection 12 of its intima. The balloon 2 is deflated. FIG. 20 illustrates the MAAC of FIG. 19 with the balloon 2 inflated and the damaged vessel wall reduced and repositioned while still allowing distal perfusion in the channels of the MAAC. This is the inflatable stent usage of the MAAC. FIG. 21 contains plane views of a MAAC. FIG. 22 contains a view similar to FIG. 1 but with a channel 20 disposed along only one side of the balloon and not around the balloon.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

In the foregoing, all temperatures are set forth uncorrected in degrees Celsius and unless otherwise indicated, all parts and percentages are by weight.

The entire disclosure of all applications, patents and publications, cited above, are hereby incorporated by reference.

The preceding can be repeated with similar success by substituting the generically or specifically described reactants and/or operating conditions of this invention for those used in the preceding description.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An autoperfusion dilatation balloon catheter useful in angioplasty comprising
    a catheter shaft,
    mounted on said shaft, an inflatable non-elastomeric balloon having an outer surface and proximal and distal ends disposed along the length of said catheter shaft, said balloon when inflated having a channel in its outer surface whereby when said balloon is fully inflated and exerts pressure on the inner surface of a blood vessel in which blood is flowing, blood continues flowing between said outer surface of said balloon and said inner surface of said blood vessel through said channel, and
    a band tightly mounted over the outside surface of said balloon on a line along the length of said catheter shaft and fixedly attached to said catheter shaft at or beyond each of said balloon proximal and distal ends, whereby said band exerts a force on said balloon outside surface directed inward toward said catheter shaft along said line when said balloon is inflated, whereby said channel is formed in said balloon outer surface when inflated.

2. The autoperfusion catheter of claim 1, wherein said channel is disposed around said outer surface of said balloon in a helical-like pattern.

3. The autoperfusion catheter of claim 2, further comprising a radially expandable, pressure distribution sleeve disposed around said balloon.

4. The autoperfusion catheter of claim 2, wherein said band maintains said balloon outer surface in compressive contact with said shaft along said line when said balloon is inflated.

5. The autoperfusion catheter of claim 1, wherein said channel is disposed along one side of said balloon and not around said balloon.

6. The autoperfusion catheter of claim 5, further comprising a radially expandable, pressure distribution sleeve disposed around said balloon.

7. The autoperfusion catheter of claim 1, wherein said band maintains said balloon outer surface in compressive contact with said shaft along said line when said balloon is inflated.

8. The autoperfusion catheter of claim 1, wherein said catheter shaft comprises an outer surface and said band is disposed in a groove recessed in said catheter outer surface along said line, whereby said band substantially does not protrude beyond said outer surface of said catheter shaft.

9. The autoperfusion catheter of claim 1, further comprising a radially expandable, pressure distribution sleeve disposed around said balloon.

10. The autoperfusion catheter of claim 1, wherein the dimensions of said at least one channel provided blood flow of a volume at least 80–100% of normal blood flow in a blood vessel, when said balloon is fully inflated in said blood vessel and exerts pressure on the inner surface of the blood vessel.

11. In a method of performing an angioplasty procedure using a dilatation balloon catheter, the improvement wherein the catheter is an autoperfusion dilatation balloon catheter useful in angioplasty comprising a catheter shaft, mounted on said shaft, an inflatable non-elastomeric balloon having an outer surface and proximal and distal ends disposed along the length of said catheter shaft, said balloon when inflated having a channel in its outer surface whereby when said balloon is fully inflated and exerts pressure on the inner surface of a blood vessel in which blood is flowing, blood continues flowing between said outer surface of said balloon and said inner surface of said blood vessel through said channel, and a band tightly mounted over the outside surface of said balloon on a line along the length of said catheter shaft and fixedly attached to said catheter shaft at or beyond each of said balloon proximal and distal ends, whereby said band exerts a force on said balloon outside surface directed inward toward said catheter shaft along said line when said balloon is inflated, whereby said channel is formed in said balloon outer surface when inflated, wherein the length of time the balloon of said catheter can safely remain inflated is increased.

12. In a method of repairing a damaged blood vessel wall using a dilatation balloon catheter as an inflatable stent, the improvement wherein the catheter is an autoperfusion dilatation balloon catheter useful in angioplasty comprising a catheter shaft, mounted on said shaft, an inflatable non-elastomeric balloon having an outer surface and proximal and distal ends disposed along the length of said catheter shaft, said balloon when inflated having a channel in its outer surface whereby when said balloon is fully inflated and exerts pressure on the inner surface of a blood vessel in which blood is flowing, blood continues flowing between said outer surface of said balloon and said inner surface of said blood vessel through said channel, and, a band tightly mounted over the outside surface of said balloon on a line along the length of said catheter shaft and fixedly attached to said catheter shaft at or beyond each of said balloon proximal and distal ends, whereby said band exerts a force on said balloon outside surface directed inward toward said catheter shaft along said line when said balloon is inflated, whereby said channel is formed in said balloon outer surface when inflated, wherein the length of time the balloon of said catheter can safely remain inflated is increased.

* * * * *

UNITED STATES PATENT AND TRADEMARK OFFICE
CERTIFICATE OF CORRECTION

PATENT NO.   : 5,295,959
DATED        : March 22, 1994
INVENTOR(S)  : Paul A. Gurbel and R. David Anderson It is certified that error appears in the above-indentified patent and that said Letters Patent is hereby corrected as shown below:

Column 3, line 50, after "possess", add --such a property; rather, as is conventional for balloon--.

Column 4, line 63, delete "Y".

Column 6, line 24, delete "o".

Column 7, line 61, delete "corresponding"

Column 8, line 34, after provided insert --.-- (period).

Column 11, line 6, delete "." and insert --;--.

Column 13, line 31, delete "provided" and insert --provide--.

Signed and Sealed this

Sixth Day of September, 1994

Attest:

BRUCE LEHMAN

*Attesting Officer*          *Commissioner of Patents and Trademarks*